United States Patent [19]

Tuccillo

[11] B 3,981,723

[45] Sept. 21, 1976

[54] WHITE GOLD ALLOY

[75] Inventor: Joseph J. Tuccillo, Norwalk, Conn.

[73] Assignee: Pennwalt Corporation, Philadelphia, Pa.

[22] Filed: June 26, 1974

[21] Appl. No.: 483,256

[44] Published under the second Trial Voluntary Protest Program on February 10, 1976 as document No. B 483,256.

Related U.S. Application Data

[63] Continuation of Ser. No. 370,496, June 15, 1973, abandoned, which is a continuation-in-part of Ser. No. 190,686, Oct. 19, 1971, abandoned.

[52] U.S. Cl. .................................. 75/165; 32/8
[51] Int. Cl.² ........................................ C22C 5/02
[58] Field of Search ............................ 75/165; 32/8

[56] References Cited
UNITED STATES PATENTS

| | | | |
|---|---|---|---|
| 1,283,264 | 10/1918 | Mowrey | 75/165 |
| 1,296,938 | 3/1919 | Fahrenwald | 75/165 |
| 1,987,451 | 1/1935 | Taylor | 75/165 X |
| 2,980,998 | 4/1961 | Coleman et al. | 32/12 |
| 3,413,723 | 12/1968 | Wagner et al. | 32/8 |
| 3,667,936 | 6/1972 | Katz | 75/134 N |
| 3,679,402 | 7/1972 | Hirschhorn | 75/165 |
| 3,767,391 | 10/1973 | Tuccillo | 75/134 C |

*Primary Examiner*—L. Dewayne Rutledge
*Assistant Examiner*—E. L. Weise

[57] ABSTRACT

A white gold alloy consisting essentially of 50–54% gold, 27–31% palladium, 11–16% silver, about 0.05–0.25% of iridium or ruthenium, and 4.5–8% of indium and tin, provided there is at least 2% indium, no more than 4.5% tin, and further provided that if there is less than about 6% indium, the alloy must contain at least 0.25% tin. The alloy meets or at least narrowly approaches the ADA Spec. No. 5 for Type IV dental casting gold alloys, and is useful for dental appliances and for the fusing of porcelain thereto for dental restorations.

9 Claims, No Drawings

WHITE GOLD ALLOY

This is a continuation of application Ser. No. 370,496, filed June 15, 1973 now abandoned, which is a continuation-in-part application Ser. No. 190,686, filed Oct. 19, 1971, now abandoned.

This invention concerns a white gold alloy useful for dental casting purposes. More particularly, this invention concerns a white gold alloy composition comprised of gold, palladium and silver and critical proportions of indium, or a combination of indium and tin, and iridium or ruthenium. The alloy has a unique combination of physical properties which make it useful in the casting of dental appliances requiring "long-span" bridges, in addition to being useful for the fusing of porcelain thereto for dental restorations having aesthetic desirability.

Certain white gold alloys are described in the literature. For example, U.S. Pat. No. 1,283,264, Oct. 29, 1918, describes an alloy of 50% gold; 15% palladium and 35% silver for use in dental, electrical and jewelry applications. British Pat. No. 683,004, Nov. 19, 1952, describes alloys useful in the manufacture of spinning nozzles comprised of 20 to 65% gold, 10 to 65% palladium and 15 to 50% silver, which may contain one or more of other metals in quantities of 0.5 to 5%, such as zinc, cadmium, magnesium, tin, copper, germanium, indium, manganese, iron, cobalt and nickel. British Pat. No. 803,379, Oct. 22, 1958, describes a jewelry alloy consisting of 75% gold; 16% palladium; 4.5% silver; 1% copper and 3.5% indium. The reduction of grain size in noble metals and their alloys by the addition of iridium or ruthenium thereto is disclosed by U.S. Pat. No. 2,143,217 and by J. P. Nielsen and J. J. Tuccillo, Journal of Dental Research, Vol. 45, No. 3, Part 2, pages 964–969, May-June, 1966. U.S. Pat. No. 3,667,936 discloses a dental alloy consisting essentially of more than 95 wt. % of a precious alloy, including 8–50% of palladium, 3–12% indium and at least 33% of gold and silver. However, this reference does not suggest the presently claimed combination of indium, or indium plus tin, with iridium or ruthenium, in the specific and limited proportions necessary in the white gold alloy of this invention.

The white gold alloy embodied herein consists essentially of the components (in percents by weight) of 50 to 54% gold; 27 to 31% palladium, 11 to 16% silver, 4.5 to 8% of indium and tin, provided there is at least 2% indium and no more than 4.5% tin, and further provided that if there is less than about 6% indium, there must be at least 0.25% tin; and from about 0.05 to about 0.25% of iridium or ruthenium. Said minor amounts of iridium or ruthenium may be based on the total of the other metals in the alloy of 100%. These grain-refining components are desirably added to the melt as a binary alloy with gold or silver. An excess of these elements will show up as undesirable white spots of undigested iridium or ruthenium in the cast alloy.

It has been discovered that the foregoing proportions of metal constituents in the alloy are essential and critical, in particular the amount of indium, or indium and tin combined, and the iridium or ruthenium content, in order to obtain the desired physical properties. For instance, the present alloy meets, or at least narrowly approaches, the requirements of American Dental Association Specification No. 5 for Type IV dental casting gold alloys. In accordance with these requirements, the hardened alloy of this invention will have a Brinell hardness number of at least about 170 and often at least 200 or higher, an ultimate tensile strength of at least about 90,000 psi., and a minimum elongation of at least about 2%. Thus, the alloy's high strength and hardness qualify the alloy for ADA Type IV classification and the important utility of being useable for long span (i.e. five units and above) bridge work.

The white gold alloys embodied herein have a melting range of about 2,100° to 2,300°F. The cast alloys are normally heat treated in a conventional manner by heating in a furnace to 1,900°F. at a rate of 75° to 100°F. per minute, holding at 1900°F. for about 10 minutes, removing the specimen from the furnace and cooling under a refractory cover.

The alloy of this invention, after the described heat treatment, will have an ultimate tensile strength on the order of about 90,000 psi. and higher, a yield strength on the order of about 70,000 psi and upwards, an elongation within the range of about 2 to 13%, preferably in the range of 7 to 13%, a Brinell hardness number of about 170 and upwards, and a crystalline grain size ranging from about 10 to 30 microns.

The following examples setting forth the physical properties of representative white gold alloys demonstrate the criticality of the present composition with regard to the attainment of the desired physical properties. All physical properties for said alloys have been measured after the above-described heat treating operation.

EXAMPLE 1

A white gold alloy is prepared composed of 52% gold, 27.9% palladium, 16.5% silver, 0.1% iridium, 3% indium and 0.5% tin. The alloy has a melting range of 2,150°–2,280°F. Ultimate tensile strength is 39,500 psi, yield strength 23,700 psi, % elongation is 11.5%, Brinell hardness No. is 88, and grain size is 33 microns. This alloy is too soft and too weak to meet the requirements of an ADA Type IV dental casting gold alloy.

EXAMPLE 2

A white gold alloy of 51% gold; 29.4% palladium; 15% silver; 0.1% iridium and 4.5% indium has an ultimate tensile strength of 61,200 psi.; a yield strength of 27,500 psi.; an elongation of 32.7% and a Brinell hardness number of 101. This alloy thus fails to meet the physical property requirements for an ADA Type IV casting alloy, in constrast to the alloys of the invention described in the following examples.

EXAMPLE 3

An alloy composed of 50.5% gold; 27.1% palladium; 16% silver; 0.1% iridium; 5.8% indium and 0.5% tin has an ultimate tensile strength of 94,500 psi.; yield strength of 74,500 psi., elongation of 5.3%, a Brinell hardness number of 204, and a melting range of 2,140° to 2,300°F.

EXAMPLE 4

An alloy of 51% gold; 29.4% palladium; 12% silver; 0.1% iridium and 7.5% indium has an ultimate tensile strength of 101,800 psi.; a yield strength of 80,000 psi., an elongation of 8.5% and a Brinell hardness number of 205.

EXAMPLE 5

An alloy composed of 51% gold; 29.4% palladium; 12% silver; 0.1% iridium; 4.5% tin and 3% indium has an ultimate tensile strength of 100,000 psi.; a yield strength of 81,000 psi.; an elongation of 2%; and a Brinell hardness number of 225.

EXAMPLE 6

A preferred alloy of this invention is prepared having the constituency; 50.9% gold; 29.5% palladium; 12% silver; 0.1% iridium and 7.5% indium. The physical properties are an ultimate tensile strength of 101,700 psi.; a yield strength of 79,800 psi., an elongation of 9.9%, and a Brinell hardness number of 205; grain size is 22 microns and melting range is 2,150°–2,335°F. When corresponding amounts of indium are replaced in further alloy preparations by 2.5% tin; 3% tin; and 4.5% tin, the general good properties of the alloy are noted, however, the alloy becomes harder and less ductile with increasing tin content, the elongation being reduced to about 2% at 4.5% tin. Thus, greater amounts of tin are not advantageous since the elongation will approach 1% which is undesirable even though good ultimate tensile strength, yield strength and hardness properties are retained.

EXAMPLE 7

A series of eleven alloys of this invention composed of 52.5% gold, 27% palladium, 16% silver, 2.5% indium, 2% tin, and 0.05% ruthenium show the following physical properties (average of the series): ultimate tensile strength of 95,000 psi.; yield strength of 73,600 psi.; elongation of 8%; Brinell hardness of 180.

EXAMPLE 8

An alloy composed of 52% gold, 27% palladium, 16% silver, 2.5% indium, 2.5% tin, and 0.05% ruthenium has an ultimate tensile strength of 113,000 psi., a yield strength of 84,000 psi., an elongation of 10% and a Brinell hardness of 208.

EXAMPLE 9

An alloy composed of 51% gold, 29.5% palladium, 12% silver, 7.5% indium and 0.05% ruthenium has an ultimate tensile strength of 101,800 psi., a yield strength of 80,000 psi., an elongation of 8.7% and a Brinell hardness of 205.

EXAMPLE 10

An alloy composed of 51% gold, 29.5% palladium, 15% silver, 4.5% indium and 0.05% ruthenium has an ultimate tensile strength of 61,000 psi., a yield strength of 27,500 psi., an elongation of 32.7% and a Brinell hardness of 101. This alloy is deficient in acceptable physical properties because of insufficient indium (and tin) content.

EXAMPLE 11

An alloy composed of 52% gold, 28% palladium, 16.5% silver, 3% indium, 0.5% tin and 0.05% ruthenium has an ultimate tensile strength of 39,500 psi., a yield strength of 23,700 psi., an elongation of 11.5% and a Brinell hardness of 88. This alloy has inadequate physical properties because of low indium and tin content.

EXAMPLE 12

An alloy composed of 50.5% gold, 27.2% palladium, 16% silver, 5.8% indium, 0.5% tin and 0.05% ruthenium has an ultimate tensile strength of 94,500 psi., a yield strength of 74,500 psi., an elongation of 5.3% and a Brinell hardness of 204.

EXAMPLE 13

This example demonstrates that the presence of iridium or ruthenium is essential to obtain the high level of physical properties exhibited herein. A representative alloy (two specimens, Alloy No. 2) falling within the scope of the present invention, containing iridium in the claimed range is prepared together with an alloy (three specimens, Alloy No. 1) of comparable composition, except without iridium addition. The alloy specimens are formulated, cast, heat-treated and evaluated as described earlier. The data and results are summarized as follows:

| Components, Weight percents | Compositions Alloy No. 1 (no iridium) | Alloy No. 2 (with iridium) |
|---|---|---|
| Gold | 51.0% | 51.0% |
| Palladium | 29.5% | 29.5% |
| Silver | 12.0% | 11.9% |
| Indium | 7.5% | 7.5% |
| Iridium | 0.0% | 0.1% |

| | Physical Properties Alloy No. 1 | | | |
|---|---|---|---|---|
| | Specimen A | Specimen B | Specimen C | Average |
| Ultimate Tensile Strength, psi | 79,000 | 84,500 | 81,000 | 81,500 |
| Yield Strength (at 2% offset), psi | 73,500 | 76,500 | 75,000 | 75,000 |
| Elongation, % | 2.5 | 3.0 | 2.0 | 2.5 |
| Grain Size, microns | 150 | 150 | 150 | 150 |

| | Alloy No. 2 | | |
|---|---|---|---|
| | Specimen A | Specimen B | Average |
| Ultimate Tensile Strength, psi | 97,000 | 106,000 | 101,500 |
| Yield Strength (at 2% offset), psi | 77,500 | 83,500 | 80,500 |
| Elongation, % | 8.0 | 9.0 | 8.5 |
| Grain Size, microns | 25 | 25 | 25 |

(The Brinell Hardness numbers of all alloys are about 200 ± 5%)

The foregoing results verify that the incorporation of a minor amount of iridium (or ruthenium) in the subject alloys provides a marked improvement in physical properties (i.e., 24.5 percent greater ultimate tensile strength, 7.3 percent greater yield strength, and 240 percent greater elongation, which gives a much tougher alloy, toughness being measured by the product of tensile strength and elongation). The finer grain size also reduces the tendency of the alloy to crack during solidification after melt-casting, and to withstand stresses encountered in dental use.

As previously mentioned, the white gold alloy of this invention is extremely well adapted for the fusing of dental procelain thereto in the preparation of restorations having an esthetic veneer of porcelain bonded to a noble metals alloy base. When the conventional porcelain to gold fusion techniques are employed using firing temperatures of from about 1,700° to about 1,950°F., the resulting bond of the dental porcelain to the gold alloy will be stronger than the porcelain itself. Accordingly, another embodiment of this invention is a dental construction (i.e., dental restoration) comprising a cast metal base of the alloy embodied herein and covering said metal base in the shape of a tooth (or teeth) and secured thereto (i.e., baked-on thereto) fused procelain compatible with the metal. By "compatible" is meant that the fused procelain has a coefficient of expansion essentially matching that (and preferably slightly less than that) of the gold alloy whereby fracture of the bond and spalling is avoided during heating and cooling cycles which the construction will encounter both during fabrication of the restoration in the dental laboratory and in ordinary service in the patient's mouth. Typical fusing porcelains used in preparing baked-on-ceramic to gold restorations and the techniques used in making such constructions are described, for example, in U.S. Pat. Nos. 3,052,982; 3,052,983; 2,980,998; and 2,861,010. The following example concisely sets forth this technique, employing a representative alloy of this invention.

The first step in fabricating the restoration is to obtain an impression of the prepared teeth, this being accomplished by the dentist who makes an impression in rubber or hydrocolloid into which a stone model is cast, thus producing a replica of the patient's mouth. A "wax-up" is designed from the stone model in which it is sought to restore the teeth as closely as possible to the original anatomy. This wax impression or pattern of the restored tooth structure is invested in a casting ring. "Investment" means that refractory material is poured around the wax pattern previously connected to a wax rod which will act as a path for the wax to be melted and flowed out of the investment, and act during casting as a path for the molten metal to flow into the space previously occupied by the wax pattern. The refractory material (usually a phosphate-bonded silica) is heated to approximately 1,300°F., after which it is removed from the oven and placed in a centrifugal casting machine. The casting is made by forcing molten metal (centrifugal force) into the cavity.

After the model has solidified and cooled to room temperature, the investment is removed from the resulting casting by sandblasting. The casting is then finished by removing any metallic or non-metallic projections that are not part of the final restoration. The surface of the model to which porcelain is to be applied is ground to shape using a ceramic bonded stone. The casting metal may then optionally be heated to a temperature of approximately 1900° (100°F. above the procelain firing temperature) in order to volatize any solid contaminants from the surface of the metal. (This heat treatment will ordinarily cause formation of a relatively dark oxide on the surface of the white gold alloy casting.) When the casting has cooled it may be immersed in hydrofluoric or hydrochloric acid to (1) remove any silica particles that may remain from previous operations and (2) remove the oxide formed during the previous thermal treatment. The casting is finally cleaned in a detergent and distilled water, followed by an alcohol rinse.

A thin coat of opaque dental porcelain (as a slurry) is painted onto the surface of the casting to be porcelainized. The casting and opaque are heated to the recommended firing temperature of the opaque, generally in a range of about 1,800°–1,850°F. (The purpose of the opaque is to mask out the underlying color of the metal so that the body and incisal porcelain which is next applied will be its true color, rather than being changed by the background metal.)

The body and incisal porcelain is then applied to build the restoration up to its final shape. The porcelain is fired to the recommended temperature, generally 1,700°–1,800°F., and then ground to final shape with a rotating stone. The final step is to glaze the surface of the procelain to produce a surface impermeable to mouth fluids and food particles. In addition, the final restoration can be stained to match the adjacent tooth color in the mouth.

I claim:

1. A white gold alloy for dental castings which is characterized by having, after heat treatment by heating to 1900°F. at a rate of 75° to 100°F. per minute and maintaining at 1900°F. for about 10 minutes and cooling, an ultimate tensile strength of at least about 90,000 psi., a yield strength of at least about 70,000 psi., and a Brinell hardness number of at least about 170, consisting essentially, in percent by weight, of 50 to 54% gold; 27 to 31% palladium; 11 to 16% silver; about 0.05 to about 0.25% of iridium or ruthenium, and a total of 4.5 to 8% of indium and tin, provided there is at least 2% indium and no more than 4.5% tin, and further provided that if there is less than about 6% indium, there must be at least 0.25% tin.

2. A dental appliance having a long-span bridge comprised of the casted alloy of claim 1.

3. An alloy in accordance with claim 1 containing 52.5% gold, 27% palladium, 16% silver, 2.5% indium and 2% tin.

4. An alloy in accordance with claim 3 which contains about 0.05% ruthenium.

5. An alloy in accordance with claim 1 containing 51% gold, 29.5% palladium, 12% silver, and 7.5% indium.

6. An alloy in accordance with claim 5 which contains about 0.1% iridium.

7. An alloy in accordance with claim 5 which contains about 0.05% ruthenium.

8. An alloy in accordance with claim 1 containing 52% gold, 27% palladium, 16% silver, 2.5% indium and 2.5% tin.

9. An alloy in accordance with claim 8 which contains about 0.05% ruthenium.

* * * * *